United States Patent [19]

Griffith

[11] Patent Number: 5,281,627
[45] Date of Patent: Jan. 25, 1994

[54] SUBSTITUTED ARGININES AND SUBSTITUTED HOMOARGININES AND USE THEREOF

[75] Inventor: Owen W. Griffith, Milwaukee, Wis.

[73] Assignee: Cornell Research Foundation, Inc., Ithaca, N.Y.

[21] Appl. No.: 889,345

[22] Filed: May 28, 1992

[51] Int. Cl.$^5$ .................................... A61K 31/195
[52] U.S. Cl. ...................... 514/565; 562/560
[58] Field of Search .................... 562/560; 514/565

[56] References Cited

U.S. PATENT DOCUMENTS

| | | | |
|---|---|---|---|
| 2,663,668 | 12/1953 | Vrat | 424/94.6 |
| 4,061,542 | 12/1977 | Demny | 435/114 |
| 4,282,217 | 8/1981 | Baglioni et al. | |
| 4,477,428 | 10/1984 | Silberling et al. | 424/52 |
| 4,477,429 | 10/1984 | Silberling et al. | 424/52 |
| 4,499,067 | 2/1985 | Silberling et al. | 424/52 |
| 4,499,068 | 2/1985 | Silberling et al. | 424/52 |
| 4,698,442 | 10/1987 | Nestor et al. | 562/560 |
| 4,734,438 | 3/1988 | Macri | 514/653 |
| 5,028,627 | 7/1991 | Kilbourn et al. | |
| 5,059,712 | 10/1991 | Griffith | |
| 5,132,453 | 7/1992 | Griffith | 562/560 |
| 5,216,025 | 6/1993 | Gross et al. | 514/565 |

FOREIGN PATENT DOCUMENTS

| | | | |
|---|---|---|---|
| 2126181 | 12/1971 | Fed. Rep. of Germany | 424/94.6 |
| 90/05199 | 9/1990 | PCT Int'l Appl. | |
| WO9104024 | 4/1991 | PCT Int'l Appl. | |

OTHER PUBLICATIONS

Gross, S. S., et al, Biochem. Biophys. Res. Commun., 178, No. 3, Aug. 15, 1991; 823-829.
Kilbourn, R. G., et al, Journal of the National Cancer Institute, vol. 82, No. 9, May 2, 1990, 772-776.
Kilbourn, R. G., et al, Biochem. Biophys. Res. Commun, 172, No. 3, Nov. 15, 1990, 1132-1138.

(List continued on next page.)

*Primary Examiner*—Michael L. Shippen

[57] ABSTRACT

Guanidino substituted arginines or homoarginines based on monoalkyl carbon-substituted ornithines or lysines, having the formula

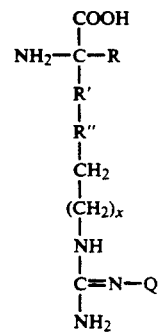

wherein R is $(CH_2)_y CH_3$ or H, R' is $CH_2$ or $C(H)(CH_2)_y CH_3$, and R" is $CH_2$ or $C(H)(CH_2)_y CH_3$, with y ranging from 0 to 5, and x is 0 or 1 and Q is an alkyl group containing from 1 to 6 carbon atoms or $NH_2$ or $NO_2$, and only one of R, R' and R" providing an alkyl substituent on the ornithine or lysine moiety. Preferred compounds are $\alpha$-methyl-$N^\omega$-methyl-DL-arginine, RS-$\beta$-methyl-$N^\omega$-methyl-DL-arginine, RS-$\gamma$-methyl-$N^\omega$-methyl-DL-arginine, $\alpha$-methyl-$N^\omega$-amino-DL-arginine, RS-$\beta$-methyl-$N^\omega$-amino-DL-arginine, RS-$\gamma$-methyl-$N^\omega$-amino-DL-arginine, $\alpha$-methyl-$N^\omega$-nitro-DL-arginine, RS-$\beta$-methyl-$N^\omega$-nitro-DL-arginine, and RS-$\gamma$-methyl-$N^\omega$-nitro-DL-arginine. A composition includes said compound together with a pharmaceutically acceptable carrier. Methods of use are directed to delivering said compound to inducible nitric oxide synthase to inhibit the ability of the enzyme to catalyze the conversion of arginine to nitric oxide, to administering said compound to inhibit pathological overproduction of nitric oxide from arginine and to administering said compound to a subject having systemic hypotension due to the pathological overproduction of nitric oxide and an $\alpha_1$ adrenergic agonist to increase blood pressure in the subject to a clinically acceptable level.

4 Claims, 2 Drawing Sheets

OTHER PUBLICATIONS

Klabunde, R. E., et al, European Journal of Pharmacology, 199:51-59, 1991.
Klabunde, R. E., et al, Biochem. Biophys. Res. Commun., 178, No. 3, Aug. 15, 1991, 1135-1140.
Schmidt, H. H. H. W., et al, Science, vol. 255, Feb. 7, 1992, 721-723.
Kilbourn, R. E., et al, Journal of the National Cancer Institute, 84(11):827-831 (1992).
Lancaster, Jr., J. R., American Scientist, 80:248-257 (1992).
Moncada, S., et al, Eur. J. Clin. Invest. 21, 361-374 (1991).
Moncada, S., et al, J. Cardopvaxci;ar jarm. 17 (suppl. 3), A1-S9 (1991).
Moncada, S., et al, Pharmacological Reviews 43(2), 109-142 (1991).
Parratt, J. R., et al, Applied Cardiopulmonary Pathophysiology, 4, 143-149 (1991).
Wang, Q., et al, Life Sciences 49, PL-55-Pl-60 (1991).
Vallance, P., et al, Lancet, 28, 997-999 (1989).
Billiar, T. R., et al, Journal of Leukocyte Biology 48:565-569 (1990).
Fostermann, U., et al, Naunyn-Schmiedeberg's Arch. Pharmacol. 340:771-774 (1989).
Gibson, A., et al, British Journal of Pharmacology, Proceedings Supplement, vol. 98, 904P, Dec. 1989.
Lambert, L. L., Life Sciences, vol. 48, pp. 69-75 (1991).
Moore, P. K., et al, British Journal of Pharmacology, Proceedings Supplement, vol. 98, 905P, Dec. 1989.
Mulsch, A., et al, Naunyn-Schmiedberg's Arch. Pharmacol. 341:143-147 (1990).
Nava, E., et al, The Lancet, vol. 338, 1555-1557 (Dec. 1991).
Palacios, M., et al, Biochemical and Biophysical Research Communications, vol. 165, No. 2, 802-809 (Dec. 15, 1989).
Rees, D D., et al, Br. J. Pharmacol., 96, 418-424 (1989).
Stuehr, D. J. and Griffith, O. W., Advances in Enzymology 65, 287-346 (1992).
Rees, D. D., et al, Br. J. Pharmacol. 101, 746-752 (1990).
Rees, D. D., "Identification of some novel inhibitors of the vascular nitric oxide synthase in vivo and in vitro" from S. Moncada, et al, eds., Nitric oxide from L-arginine; a bioregulatory system, Elsevier Science Publishers B.V. (Biomedical Division), pp. 485-487 (1990).
Aisaka, K., et al, Biochemical and Biophysic Research Communications, vol. 160, No. 2, pp. 881-886, Apr. 28, 1989.
Iyengar, R., et al, Proc. Natl. Acad. Sci, USA, vol. 84, pp. 6369-6373 Sep. 1987.
Palmer, R. M. J., et al, Nature (London), 333, pp. 664-666, 1988.
Rees, D. D., et al, Proc. Natl. Acad. Sci. USA, vol. 86, pp. 3375-3378, May 1989.
Aisaka, K., Biochemical and Biophysical Research Communications, 163, No. 2, 710-717 (Sep. 1989).
Hibbs, J. B., et al, The Journal of Immunology, 138, No. 2, 550-565 (1987).
Jackson, J. A., et al, J. Pharmacol. Expt. Ther. 209, 271-274 (1979).
Ko, R. Y. C., et al, J. Biomed. Res. 10, 249-258 (1976).
Olanoff, L. S., et al, J. Biomed. Res. 8, 125-136 (1977).
Savoka, K. V., et al, Biochem. Biophys. Acta 578, 47-53 (1979).
Blethen, S. L., et al, J. Biol. Chem., vol. 243, No. 8, 1671-1677 (1968).
Mitchell, J. A., et al, European Journal of Pharmacology, 182, 573-576 (1990).
Olken, N. M., et al, Biochem. Biophys. Res. Comm., vol. 177, No. 2, 828-833 (Jun. 14, 1991).
Stuehr, D. J., et al, Proc. Natl. Acad. Sci. USA, vol. 88, 7773-7777 (Sep. 1991).
Taylor, H., et al (ed.), Methods In Enzymology, vol. XVIIA, pp. 310-317, 335-340, Academic Press, 1970.
Yui, Y., et al, J. Biol. Chem., vol. 266, No. 19, 12544-12547, 1991.
Gross, S. S., et al, Biochemical and Biophysical Research Communications, vol. 170, No. 1, pp. 96-103, Jul. 16, 1990.
Fukuto, J. M., et al, Biochem. Biophys. Res. Commun. 168:458-465 (Apr. 1990).
Fasehun, O. A., et al, J. Pharmacol. Exp. Ther. 255, 1348-1358 (1990).
Greenstein, J. P., et al, Chemistry of Amino Acids, vol. 3, pp. 1850-1853, John Wiley & Sons, Inc., 1961.
Kilbourn, R., et al (1990), in "Nitric Oxide from L-Arginine A Bioregulatory System" (S. Moncada and E. A. Higgs, eds, pp. 61-67, Elsevier Science Publishers, Amsterdam).

OTHER PUBLICATIONS

Stuehr, D. J. et al, Synthesis of Nitrogen Oxides from L-Arginine by Macrophage Cytosol: Requirement for Inducible and Constitutive Components, *Biochem, Biophys. Res. Commun.*, (1989) vol. 161, 420–426.

Stuehr, D. J. et al., Activated Murine Macrophages Secrete a Metabolite Arginine with the Bioactivity of Endothelium-Derived Relaxing Factor and the Chemical Reactivity of Nitric Oxide, *J. Exp. Med.*, (1989) vol. 169 1011–1020.

Natanson, C. et al., Endotoxin and Tumor Necrosis Factor Challenges in Dogs Simulate the Cardiovascular Profile of Human Septic Shock, *Journal of Exp. Med.* (1989) 169:823–832.

Schmidt, H. et al., Arginine is a Physiological Precursor of Endothelium Derived Nitric Oxide, *Eur. J. of Pharmacology* (1988) 154:213–216.

Palmer, R. M. J. et al., L-Arginine is the Physiological Precursor for the Formation of Nitric Oxide in Endothelium-Dependent Relaxation, *Biochem. Biophys. Res. Commun.* (1988) 153:1251–1256.

Sakuma, I. et al., Identification of Arginine as a Precursor of Endothelium-Derived Relaxing Factor, *Proc. Natl. Acad. Sci U.S.A.* (1988) 85:8664–8667.

Hibbs, J. B. et al., Nitric Oxide: A Cytotoxic Activated Macrophage Effector Molecule, *Biochem. Biophys. Res. Commun.* (1988) 157:87–94.

Marletta, M. A. et al., Macrophage Oxidation of L-Arginine to Nitrite and Nitrate: Nitric Oxide Is an Intermediate, *Biochemistry* (1988), 27:8706–8711.

Palmer, R. M. J. et al., Nitric Oxide Release Accounts for the Biological Activity of Endothelium-Derived Relaxing Factor, *Nature* (1987) 327:524–526.

Stuehr, D. J. et al., Induction of Nitrite/Nitrate Synthesis in Murine Macrophages by BCG Infection, Lymphokines, or Interferon-$\gamma$, *J. of Immunology* (1987) 139:518–525.

Turan et al., *Acta Chimica Academiae Scientiarum Hungaricae* (1975) 85:327–332.

Kilbourn et al., $N^G$-Methyl-L-Arginine Inhibits Tumor Necrosis Factor-Induced Hypotension: Implications for the Involvement of Nitric Oxide *Proc. Natl. Acad. Sci. U.S.A.* (1990) 87: 3629–3632.

SUBSTITUTED ARGININES AND SUBSTITUTED HOMOARGININES AND USE THEREOF

This invention was made at least in part with Government support under Grant DK 37116 from National Institutes of Health.

TECHNICAL FIELD

The invention is directed to novel inhibitors of biological nitric oxide formation.

BACKGROUND OF THE INVENTION

For several decades nitroglycerin has been administered to humans as a vasodilating agent in the treatment of cardiovascular disease. It has been shown that nitroglycerin so administered is converted in the body to nitric oxide which is the pharmacologically active metabolite. Recently, nitric oxide has been shown to be formed enzymatically as a normal metabolite from arginine in vascular endothelium to provide an important component of endothelium-derived relaxing factors (EDRFs) which are currently being intensively studied as participating in regulation of blood flow and vascular resistance. Macrophages have also been shown to produce nitric oxide in the body as a component of their cell killing and/or cytostatic function.

More recently it has been established that the enzyme forming nitric oxide from arginine, i.e., nitric oxide synthase, occurs in at least two distinct forms, namely a constitutive form and an inducible form. The constitutive form is present in normal endothelial cells, neurons and some other tissues. Formation of nitric oxide by the constitutive form in endothelial cells is thought to play a role in normal blood pressure regulation The inducible form of nitric oxide synthase has been found to be present in activated macrophages and is induced in endothelial cells and vascular smooth muscle cells, for example, by various cytokines and/or microbial products It is thought that in sepsis or cytokine-induced shock, overproduction of nitric oxide by the inducible form of nitric oxide synthase plays an important role in the observed life-threatening hypotension. Furthermore, it is thought that over- production of nitric oxide by the inducible form of nitric oxide synthase is a basis for insensitivity to clinically used pressor agents such as $\alpha_1$ adrenergic agonists in the treatment of septic or cytokine-induced shock patients.

Considerable research effort has been expended to discover inhibitors for nitric oxide synthase activity. Much of this research effort has been directed at uncovering arginine antagonists to function to inhibit nitric oxide synthase activity. Most of the inhibitors uncovered thus far block not only inducible nitric oxide synthase activity but also constitutive nitric oxide synthase activity; and typically any specificity of inhibition of any particular arginine antagonist for inducible nitric oxide synthase activity is not so high that it is possible to block hypotension-causing, pathological overproduction of nitric oxide (an inducible enzyme-mediated process) to a therapeutically adequate extent (i.e. so that clinically serious hypotension that would normally occur in sepsis or cytokine-induced shock is avoided or so that pressor agent sensitivity is restored), and, at the same time, not block the physiological nitric oxide synthesis which is thought to play a role in neural function and normal blood pressure regulation (constitutive enzyme-mediated processes) and thereby avoid the toxicity (e.g., neuronal toxicity and hypertension) associated with interfering with physiological nitric oxide synthesis.

SUMMARY OF INVENTION

It is an object of the invention herein to provide novel arginine antagonists which inhibit inducible form of nitric oxide synthase in vascular smooth muscle cells and/or in other cells producing pathological amounts of nitric oxide, having a structure conducive to carrying out said inhibiting selectively, that is without inhibiting constitutive isoform of nitric oxide synthase to a physiologically undesirable degree.

The novel arginine antagonists herein are guanidino substituted arginines or homoarginines based on monoalkyl carbon-substituted ornithines or lysines, having the formula

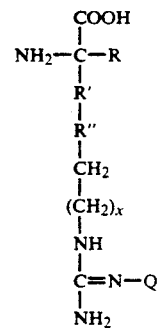

wherein R is on the α-carbon and is $(CH_2)_y CH_3$ or H, R' includes the β-carbon and is $CH_2$ or $C(H)(CH_2)_y CH_3$, and R" includes the γ-carbon and is $CH_2$ or $C(H)(CH_2)_y CH_3$, with y ranging from 0 to 5, and x is 0 or 1 and Q is on the ω nitrogen and is an alkyl group containing from 1 to 6 carbon atoms or $NH_2$ or $NO_2$, and only one of R, R' and R" provides an alkyl substituent on the ornithine (x=0) or lysine (x=1) moiety.

It is an object of another embodiment of this invention to provide a composition for inhibiting pathological overproduction of nitric oxide from arginine by inducible form of nitric oxide synthase, said composition comprising an amount of novel arginine antagonist as described above therapeutically effective to inhibit said nitric oxide synthase (and thereby prevent said pathological overproduction) and a pharmaceutically acceptable carrier.

It is an object of another embodiment of this invention to provide a method for inhibiting the ability of inducible nitric oxide synthase to catalyze the conversion of arginine to nitric oxide, said method comprising delivering to the enzyme an amount of a novel arginine antagonist as described above effective to block the catalysis.

It is an object of another embodiment of this invention to provide a method of inhibiting pathological overproduction of nitric oxide from arginine in a subject in need of said inhibition, said method comprising administering to said subject an amount of novel arginine antagonist as described above therapeutically effective to inhibit said pathological overproduction of nitric oxide.

It is an object of another embodiment of this invention to provide a method of treating a subject having systemic hypotension due to the pathological overproduction of nitric oxide from arginine, said method comprising administering to the subject an α₁ adrenergic agonist and a novel arginine antagonist as described above, the amount of novel arginine antagonist being that effective to restore vascular sensitivity to the effect of the $\alpha_1$ adrenergic agonist, the amount of $\alpha_1$ adrenergic agonist being effective to increase blood pressure to a clinically acceptable level.

DETAILED DESCRIPTION

Figure 1:
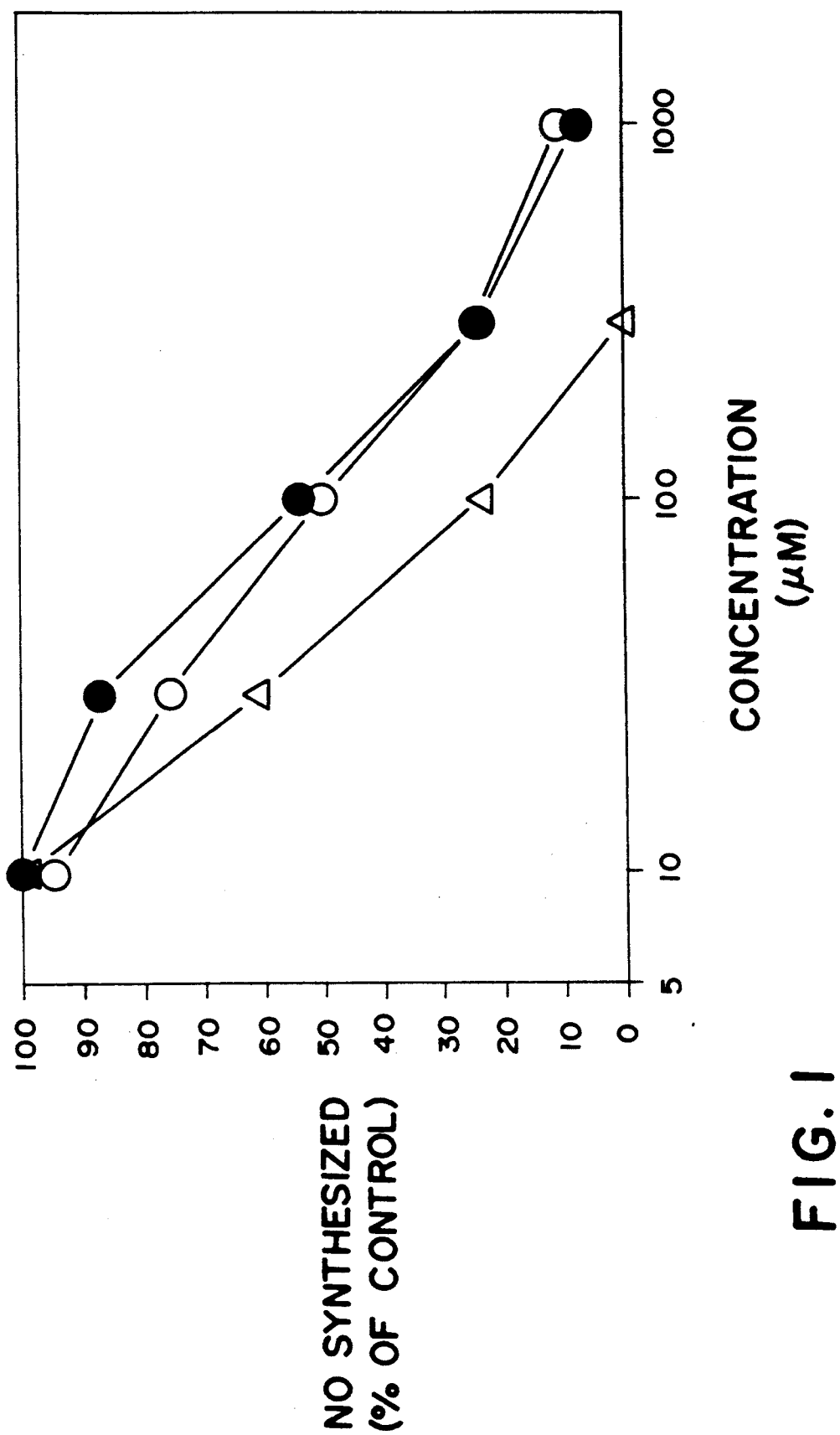
FIGS. 1 and 2 are graphs of nitric oxide synthesis activity, expressed as "NO SYNTHESIZED (% OF CONTROL)", versus concentration of inhibitor and depict the results for Example VI. NO stands for nitric oxide.

Turning now to the novel arginine antagonists herein, preferably y is 0 in the structural formula given above.

The novel arginine antagonists herein include, for example, α-methyl-N^ω-methylarginine, α-ethyl-N^ω-methylarginine, α-hexyl-N^ω-methylarginine, RS-β-methyl-N^ω-methylarginine, RS-β-propyl-N^ω-methylarginine, RS-β-hexyl-N^ω-methylarginine, RS-γ-methyl-N^ω-methylarginine, RS-γ-butyl-N^ω-methylarginine, RS-γ-pentyl-N^ω-methylarginine, RS-γ-hexyl-N^ω-methylarginine, α-methyl-N^ω-ethylarginine, α-methyl-N^ω-hexylarginine, RS-β-methyl-N^ω-propylarginine, RS-β-propyl-N^ω-propylarginine, RS-γ-butyl-N^ω-ethylarginine, RS-γ-hexyl-N^ω-hexylarginine, α-methyl-N^ω-aminoarginine, α-pentyl-N^ω-aminoarginine, RS-β-methyl-N^ω-aminoarginine, RS-β-ethyl-N^ω-aminoarginine, RS-γ-methyl-N^ω-aminoarginine, RS-γ-hexyl-N^ω-aminoarginine, α-methyl-N^ω-nitroarginine, α-butyl-N^ω-nitroarginine, RS-β-methyl-N^ω-nitroarginine, RS-β-hexyl-N^ω-nitroarginine, RS-γ-methyl-N^ω-nitroarginine, RS-γ-propyl N^ω-nitroarginine, α-methyl-N^ω-methylhomoarginine, RS-β-methyl-N^ω-methylhomoarginine, RS-γ-methyl-N^ω-methylhomoarginine, α-methyl-N^ω-aminohomoarginine, RS-β-methyl-N^ω-aminohomoarginine, RS-γ-methyl-N^ω-aminohomoarginine, α-methyl-N^ω-nitrohomoarginine, RS-β-methyl-N^ω-nitrohomoarginine, RS-γ-methyl-N^ω-nitrohomoarginine, α-ethyl-N^ω-ethylhomoarginine, RS-β-methyl-N^ω-hexylhomoarginine, α-propyl-N^ω-aminohomoarginine, RS-γ-butyl-N^ω-nitrohomoarginine.

The active form of the novel arginine antagonists herein are the L-configuration at the α-carbon as depicted in the structure above and are hereinafter designated L-isomers. The corresponding DL mixtures have activity corresponding to the amount of L-isomer present.

We turn now to the methods for providing the novel compounds herein.

The novel compounds herein where x is 0 and Q is alkyl are prepared by reacting the corresponding ornithine with N-alkyl-S-methylthiopseudouronium iodide in alkaline solution in the presence of copper salt.

The novel compounds herein where x is 0 and Q is amino are prepared by reacting the corresponding ornithine with S-methylisothiosemicarbazide in alkaline solution.

The novel compounds herein where x is 0 and Q is nitro are prepared by reacting the corresponding ornithine with S-methylthiopseudouronium iodide in alkaline solution in the presence of copper salt to form the arginine derivative and then nitrating utilizing a mixture of fuming nitric and fuming sulfuric acids (as described previously for L-arginine by Greenstein, J. P., et al, Chemistry of Amino Acids, Vol. 3, page 1852, John Wiley & Sons, Inc. 1961).

The novel compounds herein where x is 1 are made as described above for compounds with x being 0, except that the corresponding lysine is used in place of the ornithine.

We turn now to the starting material ornithines. Where R is methyl and R' and R" are CH₂, the ornithine is α-methylornithine and this is commercially available. The other α-alkylornithines are prepared from the γ-ketonitrile having the structure

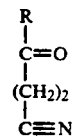

where R is as defined previously, by Strecker amino acid synthesis and reduction of the nitrile group by catalytic hydrogenation and hydrolyzing the reduced product. Alternatively α-alkylornithines can be synthesized by simple extension of the method used for the α-methylornithines as described in Demny et al U.S. Pat. No. 4,061,542. The β-alkylornithines are synthesized by reaction of ethyl acetamidomalonate with the appropriate β-substituted acrylonitrile in mildly alkaline ethanol at 25°–70° C., followed by catalytic reduction of the nitrile group, followed by acid hydrolysis. The γ-alkylornithines are synthesized in the same way as the β-alkylornithines except that α-substituted acrylonitrile is used in place of the β-substituted acrylonitrile.

We turn now to the starting material lysines. The α-alkyllysines are prepared from the β-ketonitrile having the structure

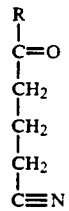

where R is as defined previously, by Stecker amino acid synthesis and reduction of the nitrile group by catalytic hydrogenation, followed by hydrolysis. The β-alkyllysines are prepared in the same way as the β-alkylornithines except that γ-bromo-γ-alkylbutyronitrile is used in place of the β-substituted acrylonitrile and 1 molar equivalent of base (e.g., sodium ethoxide) is included in the reaction mixture. The γ-alkyllysines are prepared in the same way as the γ-alkylornithines except that β-alkyl-γ-bromobutyronitrile is used in place of the α-substituted acrylonitrile and 1 molar equivalent of base (e.g., sodium ethoxide) is included in the reaction mixture. Alternative syntheses of β- and γ-alkyllysines are well known in the literature.

We turn now to the composition here comprising novel arginine antagonist and a pharmaceutically acceptable carrier. Such carriers include sterile water or physiological saline for parenteral administration. For oral administration, tablets may contain the active ingredient in admixture with conventional pharmaceutically acceptable excipients including inert diluents such as calcium carbonate, sodium carbonate, lactose and talc.

We turn now to the method herein for inhibiting the ability of inducible nitric oxide synthase to catalyze the conversion of arginine to nitric oxide, comprising delivering to the enzyme an amount of novel arginine antagonist effective to block the catalysis. Concentrations of arginine antagonists ranging from 1 μM to 10 mM are useful for this purpose. In animals (including humans) such concentrations can typically be achieved by doses ranging from 0.1 to 100 mg/kg (body weight), on the basis of contained L-isomer.

We turn now to the method herein for inhibiting pathological overproduction of nitric oxide from arginine in a subject in need of said inhibition, said method comprising administering to said subject an amount of novel arginine antagonist therapeutically effective to inhibit nitric oxide synthesis.

One group of subjects comprises those with pathologically low blood pressure.

One class within this group are those with idiopathic hypotension.

Another class within this group are those with systemic hypotension including those with septic shock (including toxic shock syndrome) or shock induced by administration of drugs including biological response modifiers such as tumor necrosis factor, interleuken-1 and interleuken-2.

Another class within this group are those with hemorrhagic shock.

Another group of subjects comprises those with immune disorders in which down regulation of nitric oxide formation is advantageous, e.g., in auto-immune disorders or in therapeutic immunosuppression for transplant purposes.

Turning now to dosage, such depends on the effect desired and the responsiveness of the individual subject. For example, for raising blood pressure, a blood pressure effective raising amount is administered. For disorders requiring immunosuppression, an immunosuppressive effective amount is administered. Generally, dosages range from 10 micrograms per kg to 100 mg/kg, preferably 1 to 10 mg/kg, are useful. The dosages are on the basis of contained L-isomer. Such dosages may be repeated as necessary to maintain blood pressure.

Administration is readily carried out, for example, by oral or parenteral routes, most preferably intravenously, with the composition including pharmaceutically acceptable carrier described above.

We turn now to the method herein for treating a subject having systemic hypotension due to the pathological overproduction of nitric oxide from arginine, said method comprising administering to the patient an $\alpha_1$-adrenergic agonist and novel arginine antagonist.

Suitable $\alpha_1$-adrenergic agonists include, for example, phenylephrine, thromboxane analogs, angiotensin II and norepinephrine.

Dosages of novel arginine antagonist to be used in combination with the $\alpha_1$-adrenergic agonists range from 0.1 to 100 mg/kg (body weight) on the basis of contained L-isomer. The dosages of $\alpha_1$-adrenergic agonists are the same as those that are pressor-effective in subjects not hyporesponsive due to overproduction of nitric oxide.

Administration is preferably by oral or parenteral routes, most preferably intravenously.

In the methods herein involving intravenous administration either bolus injection(s) or continuous infusion methods may be used.

The invention is demonstrated by the following examples.

In the Examples below amino acids were analyzed by chiral phase HPLC as described by O. W. Griffith and E. B. Campbell, Methods in Enzymology, Vol. 143, 166–172 (1987) except that flow rates were increased from 0.5 ml/min to 1.0 m./min. The elution times for various compounds are shown in the table below. Buffer A described in the table below is described in the Methods in Enzymology article. Buffer A' was a mixture of 75% Buffer A and 25% Buffer C (described in the Methods of Enzymology article).

TABLE

| Compound | Buffer | Elution time(s) (minutes) |
|---|---|---|
| L-Ornithine | A | 6.10 |
| α-Methyl-DL-Ornithine | A' | 6.92 |
| RS-β-Methyl-DL-Ornithine | A | 6.95 |
| RS-γ-Methyl-DL-Ornithine | A | 6.36 |
| $N^\omega$-Methyl-L-Arginine | A | 11.62 |
| α-Methyl-$N^\omega$-Methyl-DL-Arginine | A' | 13.80 15.06 |
| α-Methyl-$N^\omega$-Amino-DL-Arginine | A' | 12.11 |
| RS-β-Methyl-$N^\omega$-Methyl-DL-Arginine | A | 12.43 13.32 |
| RS-γ-Methyl-$N^\omega$-Methyl-DL-Arginine | A | 14.81 15.93 |

In Examples I–III below, the N,S-dimethylthiopseudouronium iodide was prepared as follows:

A 500 ml 3-neck round bottom flask was fitted with a thermometer, condenser and dropping funnel. In it was placed 25 gm of 1-methyl-2-thiourea (0.277 mol, Aldrich Chemicals) and 150 ml of acetone. The suspension was stirred magnetically as iodomethane (39.4 gm=0.2774 mol=17.2 ml) was added dropwise in small portions over 20 minutes. The temperature rose to about 35° C. The oil bath was then heated to 75°–80° C., and the solution was refluxed. During addition of iodomethane product began to precipitate. The reaction was allowed to reflux for 10 minutes and then 50 ml of ethanol was added through the condenser. The product went completely into solution, and the reaction mixture was filtered hot. The product crystallized on cooling. One hundred ml of hexane was added with stirring to the crystals, and the whole mixture was cooled to 0 degrees C. for 3 hrs. The crystals were then collected by filtration and washed with ethyl ether. The product was not hygroscopic. It was transferred to a beaker, covered and desiccated under vacuum to remove the last traces of solvent. Adding ethyl ether to the mother liquor produced a small second crop. The yield was as follows: first crop—58.1 gm; second crop—3.8 gm; overall yield—61.9 gm (95% based on 1-methyl-2-thiourea).

EXAMPLE I

Preparation of α-Methyl-$N^\omega$-Methyl-DL-Arginine

α-Methyl-DL-ornithine (1.0 gm, 5.49 mmol), Sigma Chemical Co. Catalog #M3511, was dissolved in 11 ml of conc. (25%) ammonium hydroxide. To that solution was added Cu(OAc)$_2$ H$_2$O (0.547 gm, 2.74 mmol). The mixture was allowed to stir for 2 hrs. at 25° C. To that solution was then added N,S-dimethylthiopseudouronium iodide (1.27 gm, 5.49 mmol), prepared as described above, and the reaction mixture was stirred overnight (18 hr.).

The reaction mixture was filtered to remove precipitated Cu salts and the retained solids were washed with 25% ammonium hydroxide. The combined filtrate was evaporated to dryness under reduced pressure. The residue was redissolved in water and reevaporated twice to remove all traces of ammonia. The final residue was dissolved in a minimal amount of water (5 ml) and applied to a column of Dowex 50W (H+ form, 200–400 mesh, 3×20 cm). The resin was washed with 1 L of 2.0M HCl to elute copper salts, then with 1L of 3.0M HCl to elute residual α-methyl-DL-ornithine and then with 1 L of 3.8M HCl to elute product. Fractions of 20 ml each were collected and assayed by standard HPLC amino acid analysis to identify those fractions containing α-methyl-$N^\omega$-methyl-DL-arginine (elution times of 13.80 and 15.06 minutes). Fractions containing product were evaporated to dryness under reduced pressure. The residue was dissolved in water and reevaporated twice to remove traces of HCl. The final clear oily residue was redissolved in 10 ml of water, and this stock solution was stored in the refrigerator and used for the inhibition studies. The purity of α-methyl-$N^\omega$-methyl-DL-arginine in the stock solution was >99% by HPLC; the concentration of the stock solution was determined by comparison of the HPLC peak size for aliquots of that solution to HPLC peak sizes of aliquots taken from an α-aminoisobutyric acid standard solution. The overall yield based on α-methyl-DL-ornithine was 50 to 60% in several preparations.

α-Ethyl-$N^\omega$-methyl-DL-arginine is made in the same way as the α-methyl-$N^\omega$-methyl-DL-arginine above except that an equimolar amount of α-ethyl-DL-ornithine is substituted for the α-methyl-DL-ornithine. The α-ethyl-DL-ornithine is prepared by reacting γ-ketohexanonitrile with ammonium sulfate and sodium cyanide in ethanol/water at 50° C. and reducing the nitrile group of the resulting hydantoin in acetic acid by catalytic hydrogenation over platinum oxide, followed by hydrolysis.

α-Methyl-$N^\omega$-ethyl-DL-arginine is made the same way as the α-methyl-$N^\omega$-methyl-DL-arginine above except that an equimolar amount of N-ethyl-S-methylthiopseudouronium iodide is substituted for the N,S-dimethylthiopseudouronium iodide. The N-ethyl-S-methylthiopseudouronium iodide is made the same as the N-dimethylthiopseudouronium iodide above except that 1-ethyl-2-thiourea is substituted for the 1-methyl-2-thiourea.

α-Methyl-$N^\omega$-methyl-DL-homoarginine is made in the same way as the α-methyl-$N^\omega$-methyl-DL-arginine above except that an equimolar amount of α-methyl-DL-lysine is substituted for the α-methyl-$N^\omega$-DL-ornithine. The α-methyl-DL-lysine is made in the same way as the α-ethyl-DL-ornithine except that δ-ketohexanonitrile is substituted for the γ-ketohexanonitrile.

EXAMPLE II

Preparation of RS-β-Methyl-$N^\omega$-Methyl-DL-Arginine

RS-β-methyl-DL-ornithine was prepared as follows: To a solution of 0.25 gm (11 mmol) of sodium metal in 125 ml of absolute ethanol was added 54.25 gm (250 mmol) of ethyl acetamidomalonate (purchased from Sigma Chemicals). The resulting slurry was stirred and cooled while 19 gm (23 ml; 280 mmol) of crotononitrile (Aldrich Chemicals) was added dropwise over 20 min. The solution did not clear when stirred at 25° C. for 1 hr., and the mixture was therefore heated on a warm water bath (50° C.) until it cleared. The total reaction time was 2.25 hr. The clear reaction mixture was then chilled on ice, and the solid which formed on cooling, thought to be starting material, was removed by filtration. The filtrate was evaporated to dryness under reduced pressure, and the resulting clear oil (30 gm) was dissolved in 100 ml of glacial acetic acid. That solution was placed in a 100 ml Parr bottle and was hydrogenated over 0.5 gm of $PtO_2$ at 60° C. Hydrogen absorption was brisk and complete by 5 hrs. Following hydrogenation, the solution was filtered to remove catalyst, and the filtrate was evaporated to dryness under reduced pressure. The resulting clear oil (39 gm) was dissolved in 200 ml of water and loaded onto a Dowex 50 (H+ form, 200–400 mesh) (5×30 cm). The resin was washed with 2 L water and the flow-thru was discarded. The product was eluted with 1 L of 3M ammonium hydroxide. The eluent was evaporated to dryness under reduced pressure. The oil was dissolved in 250 ml of conc. HCl, and solution was refluxed for 4 hrs. That solution was cooled and evaporated to dryness under reduced pressure. Water was added and reevaporated twice to insure removal of all HCl. Ethanol was also added and removed twice by evaporation at reduced pressure to dry the product. The final white amorphous powder weighed 11.9 gm and was pure RS-β-methyl-DL-ornithine·HCl by HPLC. The yield was 66 mmol or 26.4% based on starting ethyl acetamidomalonate.

RS-β-Methyl-DL-ornithine (5.16 gm; 30 mmol) was dissolved in 60 ml of 25% ammonium hydroxide with 3.02 gm of cupric acetate (15 mmol) and magnetically stirred for 1 hr. at 25° C. To that solution was added 7.14 gm of N,S-dimethylisothiopseudouronium iodide (30 mmol), and the solution was tightly covered with parafilm and stirred overnight. The yellow precipitate that formed was removed by filtration, and the filtrate was concentrated to an oil by evaporation under reduced pressure. Water was added to and removed from the resulting oil twice to ensure all traces of ammonia were removed. The final residue was dissolved in 20 ml of water and loaded onto a column of Dowex 50 (H+, 200–400 mesh, 2.5×30 cm). After washing the resin with 1 L of water, the amino acids were eluted with 500 ml of 3M ammonium hydroxide. The eluent was evaporated under reduced pressure to yield an oil. The oil was dissolved in 50 ml of water and adjusted to pH 3 with flavianic acid (Aldrich Chemicals). After refrigeration overnight, a yellow precipitate formed, and was collected by filtration and washed with cold water, ethanol, and ethyl ether. The yellow powder was dried under vacuum and weighed 5.23 gm. It contained 10% β-methyl-DL-ornithine.

To remove the methylornithine, the powder (5.23 gm) was suspended in 40 ml of water and the pH was adjusted to 7 with sodium hydroxide. The powder dissolved to give a yellow solution. The pH was then adjusted back to 3 with glacial acetic acid, and flavianate salt recrystallized on refrigeration. That material was collected and washed with water, ethanol and ethyl ether as described above. The recrystallization procedure was repeated two more times. The final yield of RS-β-methyl-$N^\omega$-methyl-DL-arginine flavianate was 3.5 gm. That material contained <5% methylornithine.

The flavianate was removed by suspending 3.5 gm of the yellow solid in 40 ml of water and stirring with Dowex 1 (OAc⁻ salt, 200–400 mesh). Portions (about 0.5 gm each) of Dowex were added until the solution was clear and all of the flavianate salt was dissolved.

The clear suspension was filtered to remove Dowex, and the filtrate was evaporated under reduced pressure to dryness. The resulting oil was redissolved in ethanol and that solution was also dried by evaporation. The addition and removal of ethanol was repeated 3 times. The final residue was a white, hygroscopic solid. It was collected and fully dried over $P_2O_2$ in vacuum. The product weighed 1.26 gm (5 mmol); 17% yield based on starting methylornithine. By HPLC analysis, the purity was >97% with the compound eluting at 12.43 and 13.32 minutes.

RS-$\beta$-Hexyl-N$^\omega$-methyl-DL-arginine is made in the same way as the RS-$\beta$-methyl-N$^\omega$-methyl-DL-arginine above except that an equimolar amount of RS-$\beta$-hexyl-DL-ornithine is substituted for the RS-$\beta$-methyl-DL-ornithine. The RS-$\beta$-hexyl-DL-ornithine is made the same as the RS-$\beta$-methyl-DL-ornithine above except that $\beta$-hexylacrylonitrile is substituted for crotononitrile.

RS-$\beta$-Methyl-N$^\omega$-ethyl-DL-arginine is made in the same way as the RS-$\beta$-methyl-N$^\omega$-methyl-DL-arginine above except that an equimolar amount of N-ethyl-S-methylthiopseudouronium iodide, made as described above, is substituted for the N,S-dimethylthiopseudouronium iodide.

RS-$\beta$-Methyl-N$^\omega$-methyl-DL-homoarginine is made in the same way as the RS-$\beta$-methyl-N$^\omega$-methyl-DL-arginine above except that an equimolar amount of RS-$\beta$-methyl-DL-lysine is substituted for the RS-$\beta$-methyl-DL-ornithine. The RS-$\beta$-methyl-DL-lysine is made the same way as the RS-$\beta$-methyl-DL-ornithine described above except the amount of sodium is increased to 5.75 gm and $\gamma$-bromovaleronitrile is substituted for the crotononitrile.

EXAMPLE III

Preparation of RS-$\gamma$-Methyl-N$^\omega$-Methyl-DL-Arginine

RS-$\gamma$-Methyl-DL-ornithine was made as follows: To a solution of 0.25 gm (1 mmol) of sodium metal in 125 ml of absolute ethanol was added 54.25 gm (250 mmol) of ethyl acetamidomalonate (purchased from Sigma Chemicals). The resulting slurry was stirred and cooled while 19 gm (23.7 ml; 280 mmol) of methacrylonitrile (Aldrich Chemicals) was added dropwise over 20 min. The solution did not clear when stirred at 25° C. for 1 hr., and the mixture was therefore heated on a warm water bath (50° C.) until it cleared. The total reaction time was 2.25 hr. The clear reaction mixture was then chilled on ice, and the solid which formed on cooling, thought to be starting material, was removed by filtration (weight =21.2 gm). The filtrate was evaporated to dryness under reduced pressure, and the resulting clear oil (49.05 gm) was dissolved in 100 ml of glacial acetic acid. That solution was placed in a 500 ml Parr bottle and was hydrogenated over 0.5 gm of $PtO_2$ at 60° C. Hydrogen absorption was brisk and complete by 5 hr. Following hydrogenation, the solution was filtered to remove catalyst, and the filtrate was evaporated to dryness under reduced pressure. The resulting clear oil (42.07 gm) was dissolved in 200 ml of water and loaded onto a Dowex 50 (H+ form, 200–400 mesh) (5×30 cm). The resin was washed with 2L water and the flow-thru was discarded. The product was eluted with 1 L of 3M ammonium hydroxide. The eluent was evaporated to dryness under reduced pressure. The oil was dissolved in 250 ml of conc. HCl, and solution was reluxed for 4 hr. That solution was cooled and evaporated to dryness under reduced pressure. Water was added and reevaporated twice to insure removal of all HCl. Ethanol was also added and removed twice by evaporation at reduced pressure to dry the product. The final white amorphous powder weighed 13.7 gm and was pure RS-$\gamma$-methyl-DL-ornithine·HCl by HPLC. The yield was 75 mmol or 30.0% based on starting ethyl acetamidomalonate.

RS-$\gamma$-Methyl-DL-ornithine (1.00 gm; 5.81 mmol) was dissolved in 6 ml of 25% ammonium hydroxide with 0.5% gm of cupric acetate (2.9 mmol) and magnetically stirred for 1 hr. at 25° C. To that solution was added 1.38 gm of N,S-dimethylisothiopseudouronium iodide (5.81 mmol), and the solution was tightly covered with parafilm and stirred overnight. The yellow precipitate that formed was removed by filtration, and the filtrate was concentrated to an oil by evaporation under reduced pressure. Water was added to and removed from the resulting oil twice to ensure all traces of ammonia were removed. The final residue was dissolved in 5 ml of water and loaded onto a column of Dowex 50 (H+, 200-400 mesh, 1.2×30 cm). After washing the resin with 250 ml of water, the amino acids were eluted with 250 ml of 3M ammonium hydroxide. The eluent was evaporated under reduced pressure to yield an oil. The oil was dissolved in 10 ml of water and adjusted to pH 3 with flavianic acid (Aldrich Chemicals). After refrigeration overnight, a yellow precipitate formed, and was collected by centrifugation and washed by suspension in cold water several times followed by reisolation by centrifugation. The resulting yellow powder representing RS-$\gamma$-methyl-N$^\omega$-methyl-DL-arginine flavianate salt was not characterized further and was not recrystallized. By HPLC it was >90% pure and its isomers eluted at 14.81 and 15.93 minutes.

The flavianate was removed by suspending the yellow solid in 3 ml of water and stirring with 0.5 gm Dowex 1(OAc− salt, 200–400 mesh). The clear suspension was filtered to remove Dowex, and the filtrate was evaporated under reduced pressure to dryness. The resulting oil weighed 0.86 gm (3.5 mmol); 59% yield based on starting methylornithine. By HPLC analysis, the purity was >90% and its isomers eluted at 14.81 and 15.93 minutes.

RS-$\gamma$-Propyl-N$^\omega$-methyl-DL-arginine is made in the same way as the RS-$\gamma$-methyl-N$^\omega$-methyl-DL-arginine above except that an equimolar amount of RS-$\gamma$-propyl-DL-ornithine is substituted for the RS-$\gamma$-methyl-DL-ornithine. The RS-$\gamma$-propyl-DL-ornithine is made the same way as the RS-$\gamma$-methyl-DL-ornithine except that $\alpha$-propylacrylonitrile is substituted for methacrylonitrile.

RS-$\gamma$-Methyl-N$^\omega$-ethyl-DL-arginine is made in the same way as the RS-$\gamma$-methyl-N$^\omega$-methyl-DL-arginine above except that an equimolar amount of N-ethyl-S-methylthiopseudouronium iodide, made as described above, is substituted for the N,S-dimethylthiopseudouronium iodide.

RS-$\gamma$-Methyl-N$^\omega$-methyl-DL-homoarginine is made in the same way as the RS-$\gamma$-methyl-N$^\omega$-methyl-DL-arginine except that an equimolar amount of RS-$\gamma$-methyl-DL-lysine is substituted for the RS-$\gamma$-methyl-DL-ornithine. The RS-$\gamma$-methyl-DL-lysine is made the same way the RS-$\beta$-methyl-DL-ornithine described above except that the amount of sodium is increased to 5.75 gm and $\gamma$-bromo-$\beta$-methylbutyronitrile is substituted for the methacrylonitrile.

EXAMPLE IV

Preparation of α-Methyl-N$^\omega$-Amino-DL-Arginine

S-Methylisothiosemicarbazide was prepared by reacting thiosemicarbazide and methyl iodide as follows: (The general method is described by Tomcufcik, A. S., Chemical Abstracts, 72:90113c.) In a pressure bottle 1.0 gm of thiosemicarbazide was suspended in 10 ml of absolute ethanol and to it was added 1.64 gm of iodomethane. The bottle was sealed and heated 1 hr at 105° C. A clear solution resulted. After cooling, the bottle was opened and 40 ml of ethyl acetate was added. The white crystals that formed were collected by filtration, washed with ethanol and ethyl acetate mixture (50/50) and dried under vacuum. S-Methylisothiosemicarbazide was obtained in 83% yield.

In 1.0 ml of water is dissolved 250 mg of α-methyl-DL-ornithine (1.37 mmol). To that solution was added 137 µl of 10M NaOH to generate the free base form of α-methylornithine. The solution was then heated to 80° C. and to it was added 319.1 mg of S-methylisothiosemicarbazide (1.37 mmol) in four equal portions at 30 min. intervals. Each addition was followed by the addition of 34 µl of 10M NaOH. Fifteen min. after the last addition, the reaction mixture was acidified to neutrality by addition of conc. HCl.

The crude neutral reaction mixture was applied to a small (1.0×20 cm) column of Dowex 50 (H+, 200-400 mesh). The resin was washed with a small amount of water and then eluted with, in sequence, 2.0M HCl (200 ml), 3.0M HCl (250 ml) and 3.8M HCl (250 ml). The eluent from the 3.8M HCl wash was collected in fractions and each fraction was assayed for α-methyl-N$^\omega$-amino-DL-arginine by HPLC (elution time =12.11 min). Fractions containing product were pooled and evaporated to dryness under reduced pressure. The residual oil was redissolved in a small (10 ml) volume of water and the solution was again reduced to dryness by evaporation. This procedure was repeated once more to assure that all HCl was removed. The residual oil did not crystallize and was therefore dissolved in a small volume of water (5 ml) and stored frozen as a stock solution. The concentration of the solution was determined by HPLC using solutions of α-aminoisobutyrate of known concentration as standards.

RS-β-Methyl-N$^\omega$-amino-DL-arginine is made in the same way as α-methyl-N$^\omega$-aminoarginine except that an equimolar amount of RS-β-methyl-DL-ornithine made as described above is substituted for the α-methyl-DL-ornithine.

RS-γ-Methyl-N$^\omega$-amino-DL-arginine is made in the same way as α-methyl-N$^\omega$-aminoarginine except that an equimolar amount of γ-methyl-DL-ornithine made as described above is substituted for the α-methyl-DL-ornithine.

α-Methyl-N$^\omega$-amino-DL-homoarginine is made in the same way as the α-methyl-N$^\omega$-amino-DL-arginine except that an equimolar amount of α-methyl-DL-lysine made as described above is substituted for the α-methyl-DL-ornithine.

EXAMPLE V

Preparation of α-Methyl-N$^\omega$-Nitro-DL-Arginine

α-Methyl-DL-arginine is prepared as described in Example I for α-methyl-N$^\omega$-methyl-DL-arginine except that an equimolar amount of S-methylpseudothiouronium iodide is substituted for N,S-dimethylpseudouronium iodide. α-Methyl-DL-arginine is converted into α-methyl-N$^\omega$-nitro-DL-arginine by reacting with a large molar excess of fuming nitric and sulfuric acids as described in Greenstein, J. P., et al, Chemistry of Amino Acids, Vol. 3, page 1852, John Wiley & Sons, Inc. (1961). The reaction mixture is then diluted 10-fold with water and applied to a column of Dowex 50 (H+). The resin is eluted with 10 column volumes of water to elute nitric and sulfuric acids and α-methyl-N$^\omega$-nitro-DL-arginine is then eluted with 3M ammonium hydroxide. Product containing fractions are pooled and evaporated to dryness under reduced pressure. The residue is crystallized from water.

RS-β-Methyl-N$^\omega$-nitro-DL-arginine is made in the same way as the α-methyl-N$^\omega$-nitro-DL-arginine above except that RS-β-methyl-DL-ornithine is substituted for α-methyl-DL-ornithine.

RS-γ-Methyl-N$^\omega$-nitro-DL-arginine is made in the same way as the α-methyl-N$^\omega$-nitro-DL-arginine above except that RS-γ-methyl-DL-ornithine is substituted for α-methyl-DL-ornithine.

EXAMPLE VI

Reaction mixtures were made up containing 50 µL of a working solution, 10 µL myoglobin solution (3 mg/ml), 10 µL inhibitor, 20 µL nitric oxide synthase and 10 µL water.

The working mixture was made up to contain 160 mM tris buffer, 200 µM L-arginine, 1 mM NADPH, 20 µM flavin adenine dinucleotide, 20 µM tetrahydrobiopterin in distilled water (pH adjusted to 7.6 by adding 10N NaOH).

The nitric oxide synthase was obtained as follows: Aortic smooth muscle cells were cultured by explanting segments of the medial layer of aortae from adult male Fischer 344 rats. Aortae were removed aseptically and freed of adventitial and endothelial cells by scraping both the lumenal and abluminal surfaces. Medial fragments (1-2 mm) were allowed to attach to dry Primaria 25 cm$^2$ tissue culture flasks (Falcon; Oxnard, Calif.) which were kept moist with growth medium until cells emerged. Cultures were fed twice weekly with medium 199 containing 10% fetal bovine serum, 25 mM HEPES, 2 mM L-glutamine, 40 µg/ml endothelial cell growth supplement (Biomedical Technologies; Stoughton, Mass.) and 10 µg/ml gentamycin (GIBCO; Grand Island, N.Y.). When primary cultures became confluent, they were passaged by trypsinization. Cells in passage 10-15 were seeded at 20,000/well. When the cells became confluent (density of 60-80×10$^3$ cells in a well), the medium was removed by suction and fresh medium consisting of 200 µl of RPMI 1640 (Whittaker Laboratories) containing 10% bovine calf serum, 25 mM HEPES buffer (pH 7.4), 2 mM glutamine, 80 U/ml penicillin, 80 µg/ml streptomycin, 2 µg/ml fungizone, 40 ng/ml interleukin-1 and 50 ng/ml interferon-gamma. (Under these conditions the inducible form of nitric oxide synthase was induced.)

Inhibitors were added to the reaction mixtures in concentrations in µM as specified.

Figure 2:
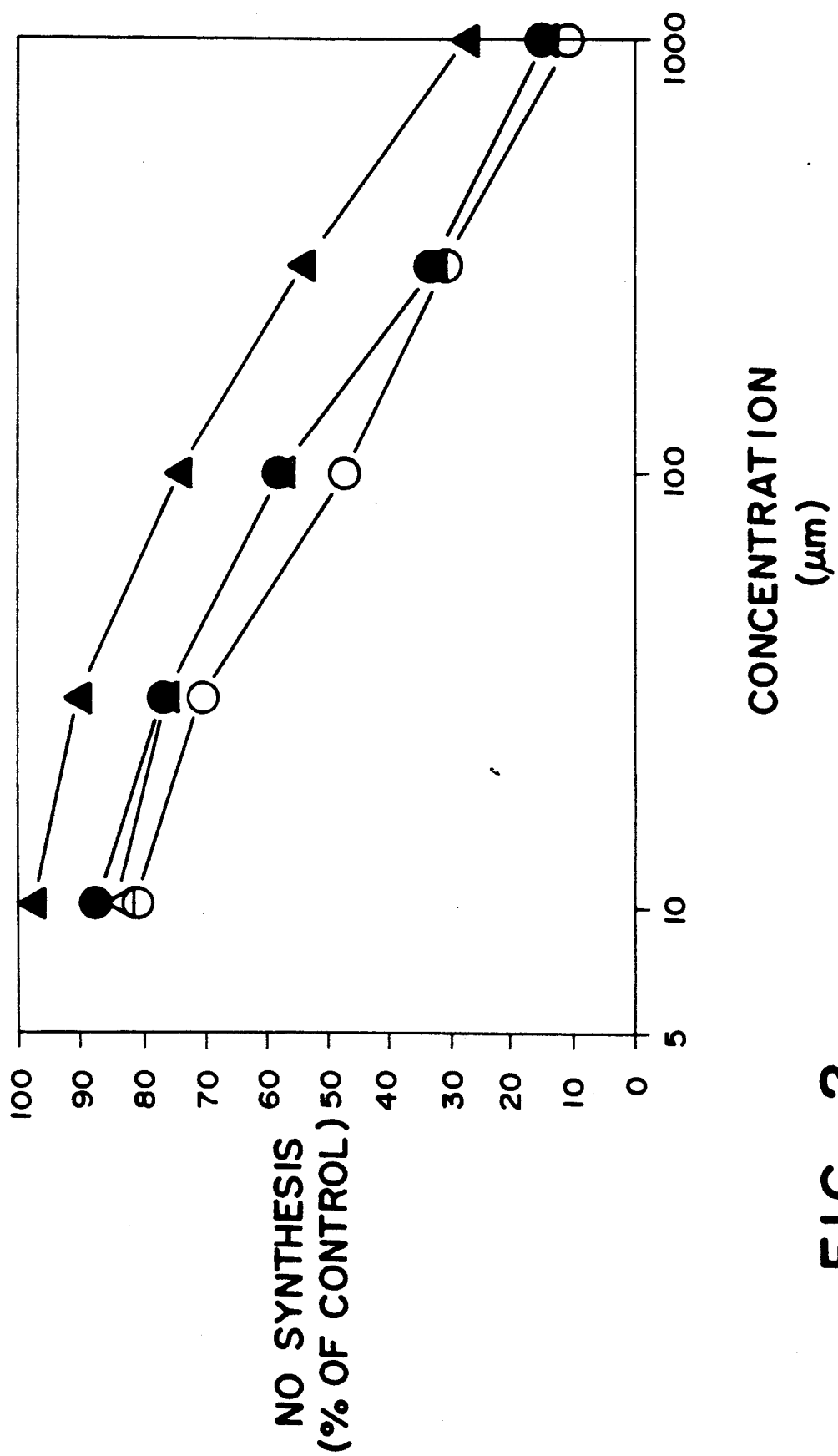

The results are shown in FIGS. 1 and 2. In FIG. 1, the open circles are for N$^\omega$-methyl-DL-arginine as inhibitor, the filled in circles are for α-methyl-N$^\omega$-methyl-DL-arginine as inhibitor and the open triangles are for α-methyl-N$^\omega$-amino-DL-arginine as inhibitor. In FIG. 2, the open circles are for N$^\omega$-methyl-DL-arginine as inhibitor, the filled in circles are for α-methyl-N$^\omega$-methyl-DL-arginine as inhibitor, the open triangles are for α-methyl-N^ω-methyl-DL-arginine as inhibitor and the filled in triangles are for γ-methyl-N^ω-methyl-DL-arginine as inhibitor. The N^ω-methyl-DL-arginine is commercially available.

The data shows that all the four novel inhibitors tested have inhibiting capability comparable to the commercially available N^ω-methyl-DL-arginine. The α-methyl-N^ω-amino-DL-arginine is shown to be about twice as effective as the commercial compound based on the concentration necessary to inhibit 50%.

EXAMPLE VII

Five conditioned mongrel dogs, designated dogs 1, 2, 3, 4 and 5, weighing 28 to 30 kgs, are studied. Care of the animals is in accordance with the recommendation of the American Association for Accreditation of Laboratory Animals [DHEW(DHHS) publication no. (NIH) 78-23, revised, 1978]. On the day of the experiment, the dogs are fasted overnight. They are anesthetized with phenobarbital (10 mg/kg). They are then intubated orally with an endotracheal tube and ventilated with a Harvard pump ventilator at a rate of 12 breaths per minute and a tidal volume of 15 ml/kg. An arterial line is percutaneously placed in the femoral artery on the day of the experiment.

Recombinant human tumor necrosis factor (TNF), specific activity $2 \times 10^7$ units/mg, is administered to each animal at a dose of 10 mcg/kg in a volume of 10 ml of phosphate buffered saline containing 2 mg/ml of dog albumin.

Within one hour blood pressure drops at least 30–40 mm Hg.

At this point one of the compounds or saline is given by bolus intravenous injection to a dog at a dosage of 20 mg/kg. α-Methyl-N^ω-methyl-DL-arginine is administered to dog 1; RS-β-methyl-N^ω-methyl-DL-arginine is administered to dog 2; γ-methyl-N^ω-methyl-DL-arginine is administered to dog 3; α-methyl-N^ω-amino-DL-arginine is administered to dog 4; and saline is administered to dog 5.

Within 3 minutes of the time of inhibitor injections, blood pressure in dogs 1, 2, 3 and 4 increases by at least 20 mm Hg. The saline injection to dog 5 shows no pressor response.

EXAMPLE VIII

To establish that nitric oxide overproduction can result in a diminished sensitivity to pressor agents, studies in a rat model of septic hypotension, i.e., the endotoxic-, pithed-rat, are performed.

Animals are either untreated (control) or treated with endotoxin (lipopolysaccharide-treated; 15 mg/kg, i.p.) 6 hours prior to their being pithed and instrumented for blood pressure recording. Prior to pithing, mean systematic arterial pressure in control rats is about 120 mm Hg. Pressure falls about 50% after pithing of control animals and is reduced to about 25% of normal in pithed endotoxin-treated animals.

Administration of phenylephrine (doses ranging from 0.1 to 10 μg/kg) or of angiotensin II (doses ranging from 0.01 to 1 μg/kg) has a strong pressor effect in pithed control rats but a negligible effect in pithed endotoxic rats.

Administration of inhibitors (the same as administered to dogs 1–4 in Example VII) 5 minutes prior to administration of pressor agents at a dose of 20 mg/kg has little effect on the pressor response to phenylephrine and angiotensin II in pithed control rats but significantly increases the response to these agents in pithed endotoxic rats. Responsiveness is restored to more than 50% of the responsiveness seen in pithed control rats.

Many variations of inventive embodiments will be obvious to those skilled in the art. Thus, the inventive embodiments are defined by the claims.

What is claimed is:

1. Guanidino substituted arginines based on monoalkyl carbon-substituted ornithines, having the formula

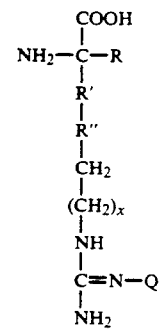

wherein R is H, R' is CH₂ or C(H)(CH₂)_yCH₃, and R" is CH₂ or C(H)(CH₂)_yCH₃, with y ranging from 0 to 5, and x is 0 and Q is methyl, and only one of R' and R" providing an alkyl substituent on the ornithine moiety and mixtures thereof with corresponding D-isomer.

2. The compound of claim 1 which is RS-β-methyl-N^ω-methyl-DL-arginine.

3. The compound of claim 1 which is RS-γ-methyl-N^ω-methyl-DL-arginine.

4. Composition for inhibiting pathological overproduction of nitric oxide from arginine by inducible form of nitric oxide synthase comprising an amount of a compound as described in claim 1 therapeutically effective to inhibit said nitric oxide synthase and thereby prevent said pathological overproduction of nitric oxide, and a pharmaceutically acceptable carrier.

* * * * *